United States Patent [19]

Taylor

[11] Patent Number: 4,695,541

[45] Date of Patent: Sep. 22, 1987

[54] ENZYMATIC DETECTION OF BACTERIAL CAPSULAR POLYSACCHARIDE ANTIGENS

[75] Inventor: Peter W. Taylor, West Haven, Conn.

[73] Assignee: Molecular Diagnostics, Inc., West Haven, Conn.

[21] Appl. No.: 696,827

[22] Filed: Jan. 31, 1985

[51] Int. Cl.$^4$ .......................... C12N 9/24; C12Q 1/00; C12Q 1/34

[52] U.S. Cl. .......................................... 435/18; 435/4; 435/29; 435/200; 435/810

[58] Field of Search .................. 435/200, 18, 4, 810, 435/29

[56] References Cited

U.S. PATENT DOCUMENTS 4,071,408  1/1978  Flashner et al. .................... 435/200
4,316,954  2/1982  Snoke et al. ........................ 435/18

*Primary Examiner*—Sidney Marantz
*Assistant Examiner*—David A. Saunders
*Attorney, Agent, or Firm*—Sprung Horn Kramer & Woods

[57] ABSTRACT

A substantially pure enzyme which hydrolyzes a polymer containing an α 2,8-linked N-acetyl neuraminic acid is obtained from K1-specific bateriophages and used for assays of bacterial polysaccharides in samples such as cerebrospinal fluid for testing for various disorders such as bacterial meningitis, septicemia, bacteremia, and the like. The enzyme may also be used therapeutically in treating such disorders by attacking cells which have an increased level of a polymer containing an α 2,8-linked N-acetyl neuraminic acid.

16 Claims, No Drawings

ENZYMATIC DETECTION OF BACTERIAL CAPSULAR POLYSACCHARIDE ANTIGENS

The present invention relates to a process for assaying biological samples for the presence of a polymer containing a particular monomer unit, to an enzyme for hydrolyzing such polymer and to the use of such enzyme therapeutically as well as diagnostically.

The majority of cases of bacterial meningitis are caused by five bacterial species, namely Streptococcus (Group B), *Escherichia coli, Haemophilus influenzae, Streptococcus pneumoniae* and *Neisseria meningitidis.* The first two organisms are the major cause of the disease in neonates; after the first ten weeks of life infections due to the latter three organisms predominate. These pathogenic bacteria characteristically produce polysaccharide capsules that constitute the major virulence determinant in meningitis, as evidenced by the fact that protection against the disease is conferred by antibodies directed against the capsular material. Although some of these bacterial species produce a wide variety of serologically-defined capsular types, relatively few serotypes possess the ability to cause meningitis. For example, of the six capsular serotypes of *H. influenzae* one, serotype b, is associated with virtually all invasive disease due to this species. The situation with *E. coli* is even more marked; although more than 70 acidic polysaccharide capsular (K) antigens are currently recognized by the WHO reference center, one K type, K1, is associated with 80–85% of all *E. coli* isolates from the cerebrospinal fluid of neonates with meningitis.

Because of the acute and life-threatening nature of the disease, and of the necessity for prompt initiation of effective therapy, rapid diagnosis of infection and reliable identification of the etiologic agent are essential components of meningitis management. Currently, several procedures are available for the detection of capsular antigens associated with many of the major meningitis pathogens; these methods include countercurrent immunoelectrophoresis, latex particle agglutination and staphylococcal coagglutination in addition to traditional direct culture methods. Although some of these methods achieve sufficient sensitivity to enable routine determination of antigen concentration over the clinically relevant range, they are limited by a high incidence of non-specific reactivity, by the additional steps required to minimize false positives and by the commercial unavailability of many of the antibody-coated reagents. Furthermore, two of the most important capsular antigens, from *E. coli* K1 strains and the structurally and serologically identical meningococcus B antigen, are such poor immunogens that practically no antisera are currently available. Consequently no standard procedure is widely applicable for the routine detection and quantitation of these important antigens in cerebrospinal fluid and other clinically relevant sample fluids.

It is accordingly an object of the present invention to provide a simple reliable way of determining the presence of certain infections, especially in newborn infants.

It is a further object of the invention to provide a method of treating such infections.

These and other objects and advantages are realized in accordance with the present invention pursuant to which there is provided a substantially pure enzyme which hydrolyzes a polymer containing $\alpha 2,8$-linked N-acetyl neuraminic acid.

In accordance with another aspect of the invention there is provided a process for assaying a biological sample for the presence of a polymer containing an $\alpha 2,8$-linked N-acetyl neuraminic acid unit which comprises contacting said sample with an enzyme which hydrolyzes such polymer, and then assaying the sample for the presence of an oligomer or monomer containing an N-acetyl neuraminic acid unit.

A kit for running such assay is also provided, the kit comprising
 (a) an enzyme which hydrolyzes a polymer containing $\alpha 2,8$-linked N-acetyl neuraminic acid, and
 (b) a reagent specific to N-acetyl neuraminic acid or a derivative thereof
wherein the polymer is a glycoprotein.

Finally, the purified enzyme may be administered therapeutically to an infected patient, thereby hydrolyzing the capsule and rendering the bacterial cell susceptible to attack by the immune system.

Specifically, applicants examined a number of K1-specific bacteriophages for the presence of enzymes able to depolymerize the K1 capsular antigen. They identified a neuraminidase that constituted part of the tail structure of K1-specific bacteriophages and purified it to apparent homogeneity as judged by polyacrylamide gel electrophoresis. The enzyme had a molecular weight of 208,000d and could be dissociated by sodium dodecylsulphate (SDS) at 100° C. to yield two polypeptides with molecular weights of 74,000d and 38,500d. Rapid hydrolysis of both the O-acetylated and non-O-acetylated forms of the K1 antigen, and of the meningococcus B antigen, was observed. The enzyme failed to release $\alpha 2,3$-, $\alpha 2,6$- and $\alpha 2,9$-linked sialyl residues from a variety of substrates of both mammalian and bacterial origin. Using an assay that discriminates between free and bound sialic acid residues, they quantitated K1 antigen over a biologically relevant concentration range. The enzyme was also therapeutically efficaceous when given to 3–5 day-old rats infected with *E. coli* K1 strains.

Many bacteriophages that undergo a lytic cycle in encapsulated bacteria possess enzyme complexes that degrade the capsule surrounding the bacterium as a necessary prerequisite for interacting with receptors on the bacterial wall or envelope. The bacterial host may be grown in a variety of culture media and seeded during the exponential phase of growth with a suspension of bacteriophage particles. Following continued incubation of the infected culture, the bacterial cells will lyse; the enzyme can be recovered from the culture supernatant either bound to bacteriophage particles or in the free, unbound state and subsequently purified by a combination of detergent treatment, density gradient ultracentrifugation, ultrafiltration, gel filtration and ion exchange chromatography.

Following determination of the substrate specificity of the purified enzyme, it was used for the assay of bacterial polysaccharide in biological samples such as cerebrospinal fluid. The enzyme (0.001–0.1 enzyme units) is added to a unit volume (50 $\mu$l–1 ml) of the sample, the pH adjusted to the optimum for enzyme hydrolysis (4.5–8.0 pH units) and the sample incubated (20°–40° C.) for 15–20 minutes. The concentration of bacterial polysaccharide in the sample may then be determined by estimating the release of sugar units from the polymer by methods that discriminate between the monomeric, or oligomeric, and polymeric states, i.e. known assays for the presence of N-acetyl neuraminic acid, e.g. a thiobarbituric acid assay. The absolute concentration is determined by comparison with a standard assay curve constructed using known amounts of polysaccharide, or by comparison with a color chart.

The polymer containing the α2,8-linked N-acetyl neuraminic acid units may be a glycoprotein or polysaccharide, homopolymeric or copolymeric. It may be bacterial capsular material such as that of *E. coli* K-1, *N. meningitidis* B or the glycoprotein of the surface of a rapidly growing cell.

Samples to be tested for such polymers include usual biological samples such as exudates, urine, plasma, serum, nasal secretions and even tissues.

The purified enzyme can also be administered therapeutically to attack cells protected by polymers containing α2,8-linked N-acetyl neuraminic acid units, thereby exposing the cell envelope to the body's immune system. Infections so treatable include bacterial meningitis, septicemia, bacteremia, and the like.

The enzyme may be administered orally but is preferably administered by injection, being dissolved in a minimum amount of saline solution and injected intravenously. As little as 5 micrograms per kg of body weight, administered once a day for several days should suffice although more or less can be used depending upon the rate of recovery and the doctor's experience.

quantified using standard agar overlay plaque assay techniques. Fractions from CsCl gradient centifugations representing free enzyme are pooled and dialysed against 0.02M $Na_3PO_4$ pH 7.5 for 24 hours with frequent buffer changes. The dialysate is concentrated to a volume of 8 ml by membrane ultrafiltration (YM5 membrane from Amicon Corporation, Danvers, Mass.; m.w. <5000), mixed with an equal volume of 10M urea containing 0.1% v/v mercaptoethanol, incubated at 37° C. for 1 hour and 3 ml aliquots applied to a 1.6×80 cm column of sephacryl S300 equilibrated with 0.02M $Na_3PO_4$, pH 7.5. The column is eluted with this buffer at a flow rate of 20 ml $cm^{-2}h^{-1}$. Fractions containing enzyme emerge soon after the void volume ($V_o$) and they are pooled and applied to a 1-6×40 cm column of DEAE-SEPHADEX previously equilibrated with 0.02M $Na_3PO_4$, pH 7.5. Fractions are eluted with a linear 0-0.5M KCl gradient and enzyme activity is found as a sharp peak eluting at a KCl concentration of 0.2-0.25M. Active fractions are pooled and concentrated; purity is assessed by SDS-polyacrylamide gel electrophoresis. The enzyme has maximal activity in the pH range 5.2-5.5.

Purification of the enzyme hereinafter identified as bacteriophage E neuraminidase is set forth n the following Table 1.

TABLE 1

| STEP | Purification of bacteriophage E neuraminidase. | | | | |
|---|---|---|---|---|---|
| | VOLUME (ml) | TOTAL PROTEIN (mg) | ENZYME[a] UNITS (U) | SPECIFIC ACTIVITY (U/mg) | PURITY (-FOLD) |
| Ammonium sulphate | 400 | 998 | 4.44 | 0.004 | 1 |
| CsCl gradient | 70 | 196 | 2.33 | 0.012 | 3 |
| Sephacryl S300 | 80 | 17.6 | 2.18 | 0.12 | 30 |
| DEAE Sephadex | 30 | 2.1 | 2.00 | 0.952 | 238 |

[a]1 unit was defined as that amount of enzyme that released 1 μmol NeuAC from LP1674 K1 polymer in 1 min at 37° C. (pH 6.5).

The invention will be further described in the following illustrative example wherein all parts are by weight unless otherwise expressed.

EXAMPLE 1

Detection and quantitation of *Escherichia coli* K1 and *Neisseria meningitidis* B antigen in cerebrospinal fluid.

(a) Purification of the enzyme

Fifteen-liter batches of Muller-Hinton medium are inoculated with *E. coli* LP1674, deposited with the ATCC on Dec. 12, 1985, ATCC No. 53351, (serotype 07:K1; Taylor, P. W., J Med. Microbiol. 9, 405–421, 1976) and incubated in a fermentor with vigorous stirring and aeration until the $OD_{578\ nm}^{1\ cm}$ reaches 0.8. K1-specific bacteriophages E deposited with the ATCC on Jan. 21, 1986, ATCC No. 40221, is added to the culture to give a multiplicity of infection of 0.25. The incubation is continued for a further 60 minutes during which time the $OD_{578\ nm}^{1\ cm}$ falls and then begins to rise again. Deoxyribonuclease I (20 mg) and $MgCl_2$ (to give a final concentration of 0.005M) are added, the lysate is allowed to cool to 4° C. and bacteria and debris are removed by centrifugation. Ammonium sulphate is then added to the supernatant to a final concentration of 50% wt/vol; following centrifugation the precipitate is dissolved in 400 ml phosphate-buffered saline pH 7.4 and enough CsCl added to give a density of 1.37 g/cc. The suspension is centrifuged to equilibrium in a fixed angle rotor (4° C., 24 hours, 32,000 rpm, Kontron TFT65) and fractions are collected by puncturing the bottom of the centrifuge tube. Infective bacteriophage particles are (b) Detection and quantitation of K1 antigen.

Cerebrospinal fluid is adjusted to pH 5.5 with 0.5M sodium acetate and 33 μl of enzyme preparation added. The mixture is incubated at 37° C. for 20 minutes. Sodium metaperiodate (0.2M in 9M $HPO_3$) is added (0.1 ml), the tubes agitated and left to stand for 20 minutes; 1 ml of 10% sodium arsenite in 0.5M sodium sulphate and 0.2M $H_2SO_4$ is then added and shaken until the solution is clear. Then 3 ml of thiobarbituric acid (0.6% in 0.5M sodium sulphate) are added and the samples boiled for 15 minutes. The tubes are cooled and 2 ml of the solution added to 2 ml of cyclohexanone, twice agitated and centrifuged for 3 minutes at 2000 rpm. The organic layer is read spectrophotometrically at $A_{549}$. Alternatively, the sensitivity can be increased by reading fluorimetrically at $A_{570}$ following excitation at $A_{549}$. The concentration is determined by reference to a standard curve prepared as above using known concentrations of purified K1 polysaccharide.

EXAMPLE 2

The specificity of the enzyme of Table 1 was examined using the substrates listed in Table 2; enzyme E was compared with commercially available neuraminidase preparations from *C. perfringens* and *V. cholera*. Compared to the bacterial enzymes, neuraminidase E exhibited a narrow substrate specificity, hydrolyzing only *E. coli* K1 antigen, the identical non-O-acetylated meningococcus B antigen and the *E. coli* K92 antigen. These three bacterial homopolymers all contain sialic acid residues linked α2-8. In contrast to the bacterial enzymes, the activity of neuraminidase E was not inhibited by O-acetylation of the K1 polymer. Interestingly, the bacteriophage enzyme did not release sialic acid from N-acetylneuramin-lactose, a widely used substrate for the detection of neuraminidase activity.

acetyl neuraminic acid unit which comprises contacting said sample with the enzyme of claim 1 and then assaying the sample for the presence of an oligomer or monomer containing an N-acetyl neuraminic acid unit.

6. A process according to claim 5, wherein the biological sample comprises cerebrospinal fluid.

7. A process according to claim 5, wherein the bio-

TABLE 2

Release of sialic acids from various substrates by neuraminidases

| Substrate[a] | Type of sialic acid linkage | O-substitution | {Enzyme (λ 547 nm)[b]} | | |
|---|---|---|---|---|---|
| | | | E | C. perfringens | V. cholera |
| E. coli K1 antigen | →8)-α-Neu5Ac—(2→ | ±7-OAc ±9-OAc | 0.20 | 0.04 | 0 |
| E. coli K1 antigen | →8)-α-Neu5Ac—(2→ | None | 0.25 | 0.26 | 0.38 |
| Meningococcus B antigen | →8)-α-Neu5Ac—(2→ | None | 0.50 | 0.51 | 0.73 |
| Meningococcus C antigen | →9)-α-Neu5Ac—(2→ | ±7-OAc ±8-OAc | 0 | 0.15 | 0.16 |
| Meningococcus Y antigen | →4)-α-D-Glu—α(2→6)Neu5Ac—(1→ | OAc, position unknown | 0 | 0 | 0 |
| Meningococcus W135 antigen | →4)-α-D-Gal—α(2→6)Neu5Ac—(1→ | None | 0 | 0 | 0 |
| E. coli K92 antigen | →9)-α-Neu5AC—α(2→9)Neu5Ac—α(2→8) Neu5Ac—α(2→8) Neu5Ac—(2→ | None | 0.16 | 0.32 | 0.31 |
| N—acetylneuramin-lactose (bovine colostrum) | Neu5Ac—α(2→3)-β-D Gal (1→4)-D-Glu Neu5Ac—α(2→6)-β-D Gal (1→4)-D-Glu | None | 0 | 1.2 | 1.3 |
| bovine brain ganglioside II | Gal β (1→3)-GalNAcβ(1→4)-Galβ(1→4)-GlcCer \| α(2-3)         \| α(2-3) Neu5Ac         Neu5Gc | None | 0 | 0.30 | 0.32 |
| bovine brain ganglioside III | Gal β (1→3)-GalNAcβ(1→4)-Galβ(1→4)-GlcCer \| α(2-3)         \| α(2-3) Neu5Gc         Neu5Ac | None | 0 | 0.30 | 0.41 |
| bovine submaxillary mucin I | Neu5Ac \} —α(2→6)-GalNac Neu5Gc | ±7-OAc ±8-OAc ±9-OAc | 0 | 0.16 | 0.10 |
| Fetal calf serum fetuin | Neu5Ac—α(2→3)-Galβ(1→3)-GalNAcα- \| α(2 6) Neu5Ac | None | 0 | 0.20 | 0.19 |
| G$_{D1a}$ ganglioside | | | 0 | 0.39 | 0 |

[a]All substrates were dissolved in Na acetate buffer pH 5.5 to a concentration of 4 mg/ml.
[b]Substrate (75 μl) was incubated for 75 min at 37° C. with 25 μl enzyme and sialic acid release determined using the TBA reaction. Values given represent formation of λ 547 nm chromogen in comparison to substrate alone. Incubation for longer periods (up to 5 h) did not result in the release of sialic acids from those substrates not hydrolysed after 75 min.

It will be understood that the specification and examples are illustrative but not limitative of the present invention and that other embodiments within the spirit and scope of the invention will suggest themselves to those skilled in the art.

What is claimed:

1. A substantially pure enzyme which hydrolyzes a polymer containing alpha 2,8-linked N-acetyl neuraminic acid, said enzyme derived from the tail structure of K-1 specific bacteriophages, said enzyme having a molecular weight of 208,000d, said enzyme characterized by not being able to release α2,3-, α2,6- and α2,9- linked sialyl residues and said enzyme having a maximal activity in the pH range of 5.2 to 5.5.

2. A kit comprising
   (a) an enzyme according to claim 1 and
   (b) a reagent specific to N-acetyl neuraminic acid or a derivative thereof.

3. A kit according to claim 2, wherein the reagent (b) includes thiobarbituric acid.

4. A kit according to claim 2, further including a color chart.

5. A process for assaying a biological sample for the presence of a polymer containing an α2,8-linked N- logical sample is an exudate, urine, plasma, serum, or nasal secretions.

8. A process according to claim 5, wherein the polymer is a polysaccharide.

9. A process according to claim 5, wherein the polymer is glycoprotein.

10. A process according to claim 5, wherein the polysaccharide is substantially homopolymeric.

11. A process according to claim 5, wherein the polysaccharide is bacterial capsular material.

12. A process according to claim 5, wherein the polysaccharide is the capsular material of E. coli K-1.

13. A process according to claim 5, wherein the polysaccharide is the capsular material of N. meningitidis B.

14. A process according to claim 5, wherein the glycoprotein is a mammalian cell surface glycoprotein.

15. A process according to claim 5, wherein the cell is a rapidly growing cell.

16. A process according to claim 5, wherein the oligomer or monomer containing an α2,8-linked N-acetyl neuraminic acid unit is determined by the thiobarbituric acid procedure.

* * * * *

UNITED STATES PATENT AND TRADEMARK OFFICE
CERTIFICATE OF CORRECTION

PATENT NO. : 4,695,541

DATED : September 22, 1987

INVENTOR(S) : Peter W. Taylor

It is certified that error appears in the above-identified patent and that said Letters Patent is hereby corrected as shown below:

| | |
|---|---|
| Col. 2, line 63 | Delete "15-20" and substitute --15-120-- |
| Col. 4, line 2 | Correct spelling of --centrifugations-- |
| Col. 4, line 11 | Delete "sephacryl" and substitute --SEPHACRYL-- |
| Col. 4, line 43 | Delete "20" and substitute --30-- |

Signed and Sealed this

Seventh Day of June, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,695,541

DATED : September 22, 1987

INVENTOR(S) : Peter W. Taylor

It is certified that error appears in the above-identified patent and that said Letters Patent is hereby corrected as shown below:

| | |
|---|---|
| Col. 6, line 56 | After "claim" delete "5" and substitute --8-- |
| Col. 6, line 58 | After "claim" delete "5" and substitute --8-- |
| Col. 6, line 60 | After "claim" delete "5" and substitute --9-- |
| Col. 6, line 62 | After "claim" delete "5" and substitute --14-- |

Signed and Sealed this

Twenty-seventh Day of June, 1989

Attest:

DONALD J. QUIGG

Attesting Officer

Commissioner of Patents and Trademarks